United States Patent [19]

Bryselbout

[11] Patent Number: 5,478,395
[45] Date of Patent: Dec. 26, 1995

[54] PROCESS FOR SUPPLYING A GAS, ESPECIALLY OF DIBORANE AND SILANE

[75] Inventor: Francis Bryselbout, Le Mesnil Saint Denis, France

[73] Assignee: L'Air Liquide, France

[21] Appl. No.: 428,715

[22] Filed: Apr. 25, 1995

Related U.S. Application Data

[62] Division of Ser. No. 151,815, Nov. 15, 1993, Pat. No. 5,447,744.

[30] Foreign Application Priority Data

Nov. 20, 1992 [FR] France ................... 92 13956

[51] Int. Cl.$^6$ .................................................. C23C 16/00
[52] U.S. Cl. .................... 118/668; 118/708; 118/712; 118/715; 73/24.05; 137/91; 137/92
[58] Field of Search ..................... 118/715, 688, 118/689, 708, 712; 73/24.05; 137/4, 91, 92

[56] References Cited

U.S. PATENT DOCUMENTS 4,369,031  1/1983  Goldman et al. .................. 432/198
4,546,016  10/1985  Kern ................................ 427/255.3
5,190,913  3/1993  Higashiyama et al. ............... 118/690

FOREIGN PATENT DOCUMENTS 2124767  2/1984  United Kingdom .

*Primary Examiner*—Richard Bueker
*Attorney, Agent, or Firm*—Burns, Doane, Swecker & Mathis

[57] ABSTRACT

A process for supplying a gas to a reactor comprising the steps of:
(i) continuously measuring density of the gas, the gas including at least one component which is susceptible to formation of an undesired side product as shown by a variation in density of the gas; and
(ii) modifying feed conditions of the gas if formation of the undesired side product is shown by a variation in the density of the gas.

The process can be employed to continuously monitor the content of diborane ($B_2H_6$) in a mixture with silane ($SiH_4$) in a process for producing a borophosphosilicate glass.

An apparatus for supplying a gas to a reactor is also disclosed.

5 Claims, 1 Drawing Sheet

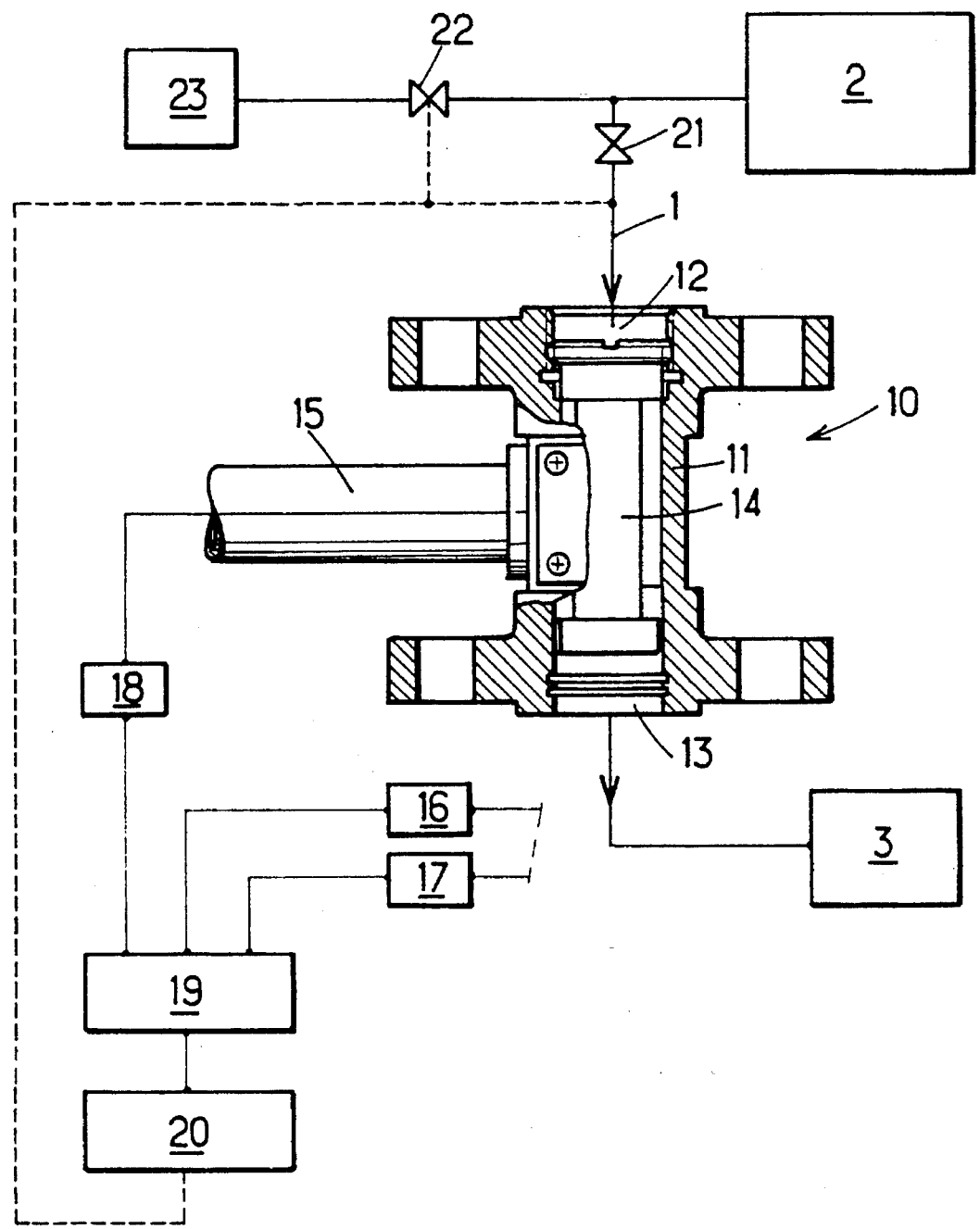

PROCESS FOR SUPPLYING A GAS, ESPECIALLY OF DIBORANE AND SILANE

This application is a divisional, of application No. 08/151,815, filed Nov. 15, 1993 now U.S. Pat No. 5,447,744.

BACKGROUND OF THE INVENTION

The present invention relates to the supplying of gas, such as a gaseous mixture based on diborane ($B_2H_6$) and of silane ($SiH_4$), destined for a reactor for growing layers of glass having a base of boron, phosphate, silicate (BPSG) ("boro-phospho-silicate glass) beginning with an initial feed of $B_2H_6/SiH_4$ in determined proportions.

It is known that this type of mixture is modified with time by virtue of the tendency of diborane ($B_2H_6$) to be transformed to higher boranes, notably those such as tetraborane ($B_4H_{10}$), pentaborane 11 ($B_5H_{11}$) which, on one hand, release hydrogen ($H_2$) and, on the other hand, are sometimes transformed to a liquid or even solid form which is not transferred with the gaseous flow. As a result, even when starting from perfectly suitable starting materials, the mixture transferred to the reactor is of improper composition notably, the mixture being of lower boron content, which forestalls against proper growing of the BPSG glass layer. This is the reason that, currently, analyses of the gaseous mixture being transferred to the reactor are carried out such as by chromatography which is not very practical because such method is discontinuous and requires frequent recalibration.

SUMMARY AND OBJECTS OF THE INVENTION

The present invention has as its goal the perfecting of this measurement by substituting therefore a method of completely different type, which is particularly well adapted to the type of application discussed above and which is reliable, continuous, simple and by virtue of which there is permitted an immediate correction, in the event of a deviation in the measured value of the content of $B_2H_6$ as compared to the consigned value.

These objects are attained, according to the invention, by continuously measuring the density of the gas or mixture and subsequently determining the variation of the composition, in particular of the content of $B_2H_6$ in a manner such that, if necessary, the conditions of gaseous feeding of the gas or notably of the mixture ($B_2H_6$) ($SiH_4$) ($H_2$) can be modified. The measurement of the density is preferably carried out by means of a gaseous density meter, of the type comprising a vibrating tube which is under the effect of electrical excitation, the frequency of the vibration depending on the density of the mixture crossing said vibrating tube, and then by processing the frequency information, optionally as a function of other information such as the pressure and temperature of the gaseous mixture, in order to continuously determine the value of the density of said mixture.

Information such as the density can be used in order to modify the conditions of feeding, particularly of the mixture $B_2H_6$-$SiH_4$, for example by controlling the flow of gas or the flow of the gaseous mixture and/or by combining it with a additional corrector flow stream, for example one having a diborane ($B_2H_6$) base in combination with an inert gas.

The invention also relates to the implementation of this process.

It is noted that although the present method focusses primarily on a process wherein a diborane gas is fed to a reactor in order to produce a borophosphosilicate glass, it is equally applicable to other processes wherein a gaseous feedstock is susceptible to side reactions forming undesired side products, such side products causing a change in the density of the gas which can be monitored so that, if necessary, adjustments in the feed materials can be carried out.

Thus, in a first aspect, the present invention relates to a process for supplying a gas to a reactor comprising the steps of:

(i) continuously measuring the density of the gas, the gas including at least one component which is susceptible to formation of an undesired side product as shown by a variation in density of the gas; and (ii) modifying feed conditions of the gas if formation of the undesired side product is shown by a variation in the density of the gas.

In a more preferred aspect, the present invention relates to a process for supplying a gas comprising a mixture of $B_2H_6$ and $SiH_4$ to a reactor for growing layers of borophosphosilicate glass comprising the steps of:

(i) continuously measuring the density of the gas by (a) passing a stream of the gas across a vibrating tube under the effect of electrical excitation; and (b) measuring the density of the gas as a function of frequency of the vibrating tube, a variation in density of the gas being indicative of the formation of undesired side products of $B_2H_6$ including higher boranes; and, if formation of higher boranes is shown by a variation in density of the gas, (ii) modifying feed conditions of the gas.

In another aspect, the present invention relates to an apparatus for supplying a gas to a reactor comprising;

(i) a reservoir including a stock material which is a gas;

(ii) a reactor into which the gas is fed;

(ii) an input conduit between the stock material reservoir and the reactor, the input conduit being provided with a means for continuously measuring density of the gas, a variation in density of the gas being indicative of formation of an undesired side product in the gas; and (iv) means for modifying feed conditions of the gas in response to formation of the undesired side product as shown by a variation in the density of the gas.

With the foregoing as well as other objects, advantages, and features of the invention that will become hereinafter apparent, the nature of the invention may be more clearly understood by reference to the following Detailed Description of Preferred Embodiments, the FIGURE, and the appended claims.

DESCRIPTION OF THE DRAWING

The FIGURE depicts a cross-sectional view of the density meter of the invention as pan of a schematic illustration of the overall process of the invention.

DETAILED DESCRIPTION OF PREFERRED EMBODIMENT

Below there is set forth in detail a preferred embodiment for carrying out the process in the reference drawing, which is now discussed in detail.

A conduit (1) links a reservoir of stock material (2) containing an initial gaseous mixture comprising diborane and silane to a utilization reactor (3). On the conduit (1) is mounted a gaseous density meter (10) having a frame (11) incorporating, between an intake (12) and an output (13), a vibrating tube (14) under the effect of an electrical excitation via a conductor (15), all of which are associated with a pressure gauge (16) and a temperature gauge (17). The gaseous density meter (10) including the vibrating tube (14) is commercially available from SARATOSA AUTOMATION. The precise type which has been used for the present invention is type FD 771 EBZT 4. It is noted that the supplier of such device provides the requisite information for determining density of a gas based on the frequency of vibration of the tube.

While the temperature and the pressure of the gaseous stream are advantageously continuously monitored, such measurement is not essential as there typically will not occur over the course of a process very wide variations therein. For this reason, it is the measurement of the density of the stream based on the frequency of vibration of the vibrating tube which is the most important measurement. The frequency of vibration of the tube (14) is displayed on a frequency meter (18), the information relating to frequency as well as that relating to pressure and temperature being processed in a processing unit (19) in order to calculate and display a density value and, if necessary, to in addition be transferred in a comparator (20) of the displayed value which is used to modify the opening of a valve (21) in the conduit (1), and/or open more or less the valve (22) controlling the flow of additional diborane starting from an auxiliary stock (23) of a mixture of diborane and inert gas (nitrogen, argon).

By way of example, there is given in the table below for a mixture $B_2H_6/SiH_4/H_2$ the content in hydrogen (% $H_2$) determined starting from pressure readings (in bars), from temperature readings (°C.), and of measured frequency μs) determining a density thus permitting calculation of the hydrogen content. It should be apparent that calculation of the hydrogen content permits calculation of the content of diborane in the mixture. These calculations can be carried out using classical thermodynamical concepts by relating, at given conditions of temperature and pressure, the density of the mixture to the partial densities of each component, taking into account data such as the constant of gases "R", the compressibility factors "Z" of each gas (that are given in tables as a function of pressure and temperature), and also the conversion factor "λ" of the decomposition reactions ($\lambda B_2H_6 H_2$) etc. For example, in the case of ($SiH_4$, $B_2H_6$) as the original feed, one can designate the components as follows:

| Silane | α |
|---|---|
| Diborane | β |
| Hydrogen | γ | wherein α, β and γ are in volume and wherein α+β+γ=s. As the mixture changes, it is evidenced by a change in the density "ρ", the percent $H_2$ of this new mixture is as follows:

$$\%H_2 = \frac{\alpha A + (\beta + \lambda\gamma)B}{\alpha(s-\lambda)A + (\beta + \lambda\gamma + \lambda\alpha)B + (\alpha + \beta + \lambda\gamma)C}$$

wherein λ= the conversion factor of the reaction (1 <λ<3).

$A = \rho_{0,SiH4} - RZ_{SiH4}\rho$ $B = \rho_{0,B2H6} - RZ_{B2H6}\rho$ $C = RZ_{H2}\rho - \rho_{0,H2}$ wherein $\rho_{0,SiH4}$, $\rho_{0,B2H6}$, and $\rho_{0,H2}$ represent the densities of each constituent at "normal" conditions (0° C., 1 atm.) and wherein $Z_i$ represents the compressibility factors for each constituent and wherein R represents the gas constant.

It is the above correlation which enables the density calculated using the process of the invention to be used in determining how to adjust a feedstream, if necessary, due to transformation of the desired diborane feed into heavier non-desired boranes.

| Hour | Pressure bar | Temperature °C. | Frequency μs | Flow cc/min | Density $B_2H_6/SiH_4/H_2$ | % $H_2$ |
|---|---|---|---|---|---|---|
| 07:02:13 | 3.352 | 18.6 | 373.3318 | 199.5 | 1.420213 | .7990299 |
| 07:03:39 | 3.353 | 18.6 | 373.3384 | 199.5 | 1.419841 | .8267524 |
| 07:05:04 | 3.361 | 18.6 | 373.3621 | 199.4 | 1.419879 | .8238842 |
| 07:06:31 | 3.354 | 18.6 | 373.3465 | 199.4 | 1.419862 | .8251541 |
| 07:07:56 | 3.353 | 18.6 | 373.3474 | 199.5 | 1.420088 | .8083447 |
| 07:09:22 | 3.361 | 18.6 | 373.3694 | 199.4 | 1.420316 | .7913489 |
| 07:10:48 | 3.35 | 18.7 | 373.3328 | 199.4 | 1.420167 | .8024486 |
| 07:12:14 | 3.353 | 18.7 | 373.3368 | 199.4 | 1.420599 | .7703219 |
| 07:13:41 | 3.356 | 18.7 | 373.3415 | 199.4 | 1.42063 | .7690131 |
| 07:15:06 | 3.353 | 18.7 | 373.3402 | 199.4 | 1.42018 | .8014629 |
| 07:16:32 | 3.35 | 18.7 | 373.3314 | 199.4 | 1.420238 | .7972096 |
| 07:17:58 | 3.354 | 18.7 | 373.336 | 199.4 | 1.420184 | .8011966 |
| 07:19:24 | 3.35 | 18.7 | 373.3373 | 199.4 | 1.420401 | .7850533 |
| 07:20:50 | 3.352 | 18.7 | 373.3374 | 199.4 | 1.420518 | .7763334 |
| 07:22:16 | 3.349 | 18.7 | 373.3308 | 199.4 | 1.420447 | .7815724 |
| 07:23:42 | 3.352 | 18.7 | 373.328 | 199.5 | 1.420415 | .7839788 |
| 07:25:08 | 3.345 | 18.7 | 373.3081 | 199.5 | 1.420134 | .804926 |
| 07:26:34 | 3.348 | 18.7 | 373.3202 | 199.5 | 1.420195 | .800353 |
| 07:27:59 | 3.347 | 18.7 | 373.3164 | 199.4 | 1.420172 | .8021111 |
| 07:29:25 | 3.345 | 18.7 | 373.3018 | 199.4 | 1.420145 | .9040913 |
| 07:30:52 | 3.343 | 18.7 | 373.3015 | 202.2 | 1.420177 | .8017116 |
| 07:32:17 | 3.348 | 18.7 | 373.309 | 199.4 | 1.420302 | .7923879 |
| 07:33:43 | 3.344 | 18.8 | 373.3008 | 199.4 | 1.420213 | .7990122 |

-continued

| | | Temperature | | | Density | |
|---|---|---|---|---|---|---|
| Hour | Pressure bar | °C. | Frequency μs | Flow cc/min | $B_2H_6/SiH_4/H_2$ | % $H_2$– |
| 07:35:09 | 3.34 | 18.8 | 373.2899 | 199.4 | 1.420393 | .7856215 |
| 07:36:35 | 3.336 | 18.8 | 373.2789 | 199.4 | 1.420628 | .7681285 |
| 07:38:01 | 3.337 | 18.8 | 373.2755 | 199.4 | 1.420274 | .794519 |
| 07:39:27 | 3.338 | 18.8 | 373.2745 | 199.4 | 1.420701 | .7627208 |
| 07:40:53 | 3.337 | 18.8 | 373.2733 | 199.4 | 1.420268 | .7949275 |
| 07:42:19 | 3.337 | 18.8 | 373.2708 | 199.4 | 1.420457 | .7808532 |
| 07:43:44 | 3.334 | 18.8 | 373.2673 | 199.4 | 1.420311 | .7917485 |
| 07:45:11 | 3.335 | 18.8 | 373.2741 | 199.4 | 1.42041 | .7843606 |
| 07:46:37 | 3.338 | 18.8 | 373.2753 | 199.4 | 1.420066 | .8099786 |
| 07:48:02 | 3.342 | 18.8 | 373.2851 | 199.4 | 1.420515 | .7765376 |
| 07:49:28 | 3.332 | 18.8 | 373.2645 | 199.4 | 1.420063 | .8102361 |
| 07:50:54 | 3.333 | 18.8 | 373.2585 | 199.4 | 1.420448 | .7815546 |
| 07:52:20 | 3.329 | 18.8 | 373.2497 | 199.4 | 1.420441 | .7820608 |
| 07:53:46 | 3.332 | 18.8 | 373.2585 | 199.5 | 1.420482 | .7789707 |
| 07:55:12 | 3.332 | 18.8 | 373.2602 | 199.4 | 1.420282 | .7939063 |
| 07:56:38 | 3.33 | 18.8 | 373.2485 | 199.4 | 1.420051 | .811133 |
| 07:58:04 | 3.329 | 18.9 | 373.2466 | 199.5 | 1.420538 | .7748504 |
| 07:59:30 | 3.332 | 18.9 | 373.2489 | 199.4 | 1.420727 | .7607139 |
| 08:00:56 | 3.327 | 18.9 | 373.2392 | 199.4 | 1.420414 | .7840853 |
| 08:02:22 | 3.328 | 18.9 | 373.2387 | 199.4 | 1.420523 | .7759693 |
| 08:03:48 | 3.328 | 18.9 | 373.2393 | 199.4 | 1.420513 | .7766975 |
| 08:05:14 | 3.326 | 18.9 | 373.2292 | 199.4 | 1.420829 | .7531573 |
| 08:06:40 | 3.324 | 18.9 | 373.2231 | 199.4 | 1.420798 | .7554749 |
| 08:08:06 | 3.323 | 18.9 | 373.2176 | 199.4 | 1.42029 | .7933025 |
| 09:09:32 | 3.319 | 18.9 | 373.2126 | 199.4 | 1.42031 | .791784 |
| 09:10:58 | 3.322 | 18.9 | 373.2158 | 199.4 | 1.420668 | .7651538 |
| 08:12:23 | 3.319 | 18.9 | 373.2078 | 199.5 | 1.420544 | .7743798 |
| 08:13:49 | 3.322 | 18.9 | 373.2116 | 199.4 | 1.420047 | .811426 |
| 08:15:16 | 3.319 | 18.9 | 373.2003 | 199.4 | 1.420154 | .803452 |
| 08:16:41 | 3.317 | 18.9 | 373.1939 | 199.4 | 1.420165 | .8026262 |
| 08:18:07 | 3.317 | 18.9 | 373.199 | 199.4 | 1.420003 | .814676 |
| 08:19:33 | 3.319 | 18.9 | 373.2029 | 199.4 | 1.419958 | .8180147 |
| 08:21:00 | 3.315 | 19 | 373.1924 | 199.4 | 1.420605 | .7698156 |
| 08:22:26 | 3.315 | 19 | 373.1944 | 199.4 | 1.420534 | .7750991 |

Although only preferred embodiments have been specifically illustrated and described above, it will be appreciated that many modifications and variations of the invention are possible in view of the above teachings without deviating from the spirit and intended scope of the invention.

What is claimed is:

1. An apparatus for supplying a gas to a reactor comprising;

(i) a reservoir including a stock material which is a gas;
   (ii) a reactor into which said gas is fed;
   (iii) an input conduit between said stock material reservoir and said reactor, said input conduit being provided with a means for continuously measuring density of said gas, a variation in density of said gas being indicative of formation of an undesired side product in said gas; and
   (iv) means for modifying feed conditions of said gas in response to formation of the undesired side product as shown by a variation in the density of said gas.

2. The apparatus according to claim 1 wherein said means for measuring density disposed between said stock material reservoir and said reactor comprises:

(i) a vibrating tube under the effect of electrical excitation across which is passed said gas;
   (ii) means for calculating the density of said gas as a function of frequency of said vibrating tube.

3. The apparatus according to claim 2 further comprising means for measuring temperature and pressure of said gas, the density of said gas being determined in said calculating means by using said measured temperature and pressure in addition to using said measured frequency of said vibrating tube.

4. The apparatus according to claim 3 wherein said means for calculating the density of said gas based on the frequency of the vibrating tube, the measured temperature and the measured pressure is an electronic unit.

5. The apparatus according to claim 1 wherein said means for modifying feed conditions of said gas in response to formation of the undesired side product, as shown by a variation in the density of said gas, comprises:

(i) a comparator which compares the measured density values of said stock material to a consigned value; and
   (ii) a reaction loop acting on the flow of the stock material and/or an additional corrector flow in order to reduce all variations of the measured density values of said stock material as compared to consigned values as determined in said comparator.

* * * * *